United States Patent
Bovo

(10) Patent No.: US 7,347,209 B2
(45) Date of Patent: Mar. 25, 2008

(54) FREE BREATHING APPARATUS

(76) Inventor: Peter J. Bovo, 5 Gardengate Ct., Columbus, NJ (US) 08022

( * ) Notice: Subject to any disclaimer, the term of this patent is extended or adjusted under 35 U.S.C. 154(b) by 0 days.

(21) Appl. No.: 11/332,326

(22) Filed: Jan. 17, 2006

(65) Prior Publication Data

US 2006/0169285 A1    Aug. 3, 2006

Related U.S. Application Data

(60) Provisional application No. 60/645,515, filed on Jan. 20, 2005.

(51) Int. Cl.
- *A61G 10/00* (2006.01)
- *A61M 16/00* (2006.01)
- *A62B 7/10* (2006.01)
- *A62B 23/02* (2006.01)

(52) U.S. Cl. ............ 128/206.11; 128/207.18; 128/207.11; 128/206.18

(58) Field of Classification Search ........... 128/206.11, 128/206.12, 206.18, 206.27, 207.13, 207.18, 128/848, 858, 206.19, 204.45; 606/161, 606/162, 198, 199

See application file for complete search history.

(56) References Cited

U.S. PATENT DOCUMENTS

| | | | | |
|---|---|---|---|---|
| 390,027 | A * | 9/1888 | Locke | 128/206.11 |
| 5,417,205 | A * | 5/1995 | Wang | 128/206.11 |
| 6,561,188 | B1 * | 5/2003 | Ellis | 128/206.11 |
| 6,562,057 | B2 * | 5/2003 | Santin | 606/199 |
| 6,679,265 | B2 * | 1/2004 | Strickland et al. | 128/207.18 |
| 6,684,882 | B1 * | 2/2004 | Morine | 128/206.11 |
| 6,978,781 | B1 * | 12/2005 | Jordan | 128/206.11 |
| 6,981,501 | B2 * | 1/2006 | Michaels | 128/206.11 |
| 2005/0066972 | A1 * | 3/2005 | Michaels | 128/206.11 |

\* cited by examiner

*Primary Examiner*—Patricia Bianco
*Assistant Examiner*—Nihir Patel
(74) *Attorney, Agent, or Firm*—Charles I. Brodsky

(57) ABSTRACT

Tubular elements inserted for enhanced breathing into the nasal passages of a wearer to increase air flow include a bridge coupling between the elements of a spring-like rigidity to spread the elements towards their quiescent obtuse angle spread before insertion, supplemented by the stretching action afforded by a strap wrapped from opposing outside surfaces of the tubular elements around the wearer's head for added securement in an adjustable fit.

8 Claims, 5 Drawing Sheets

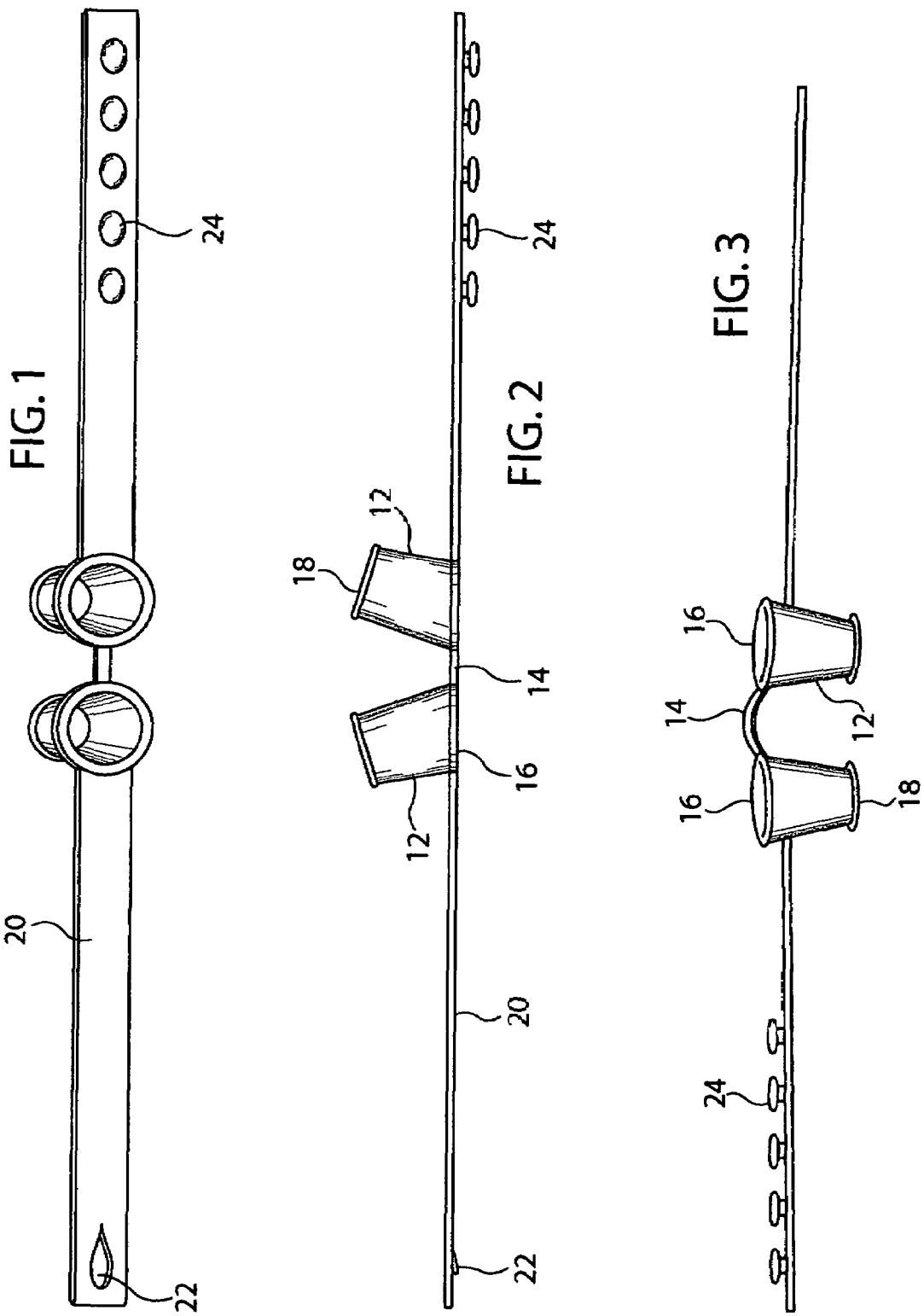

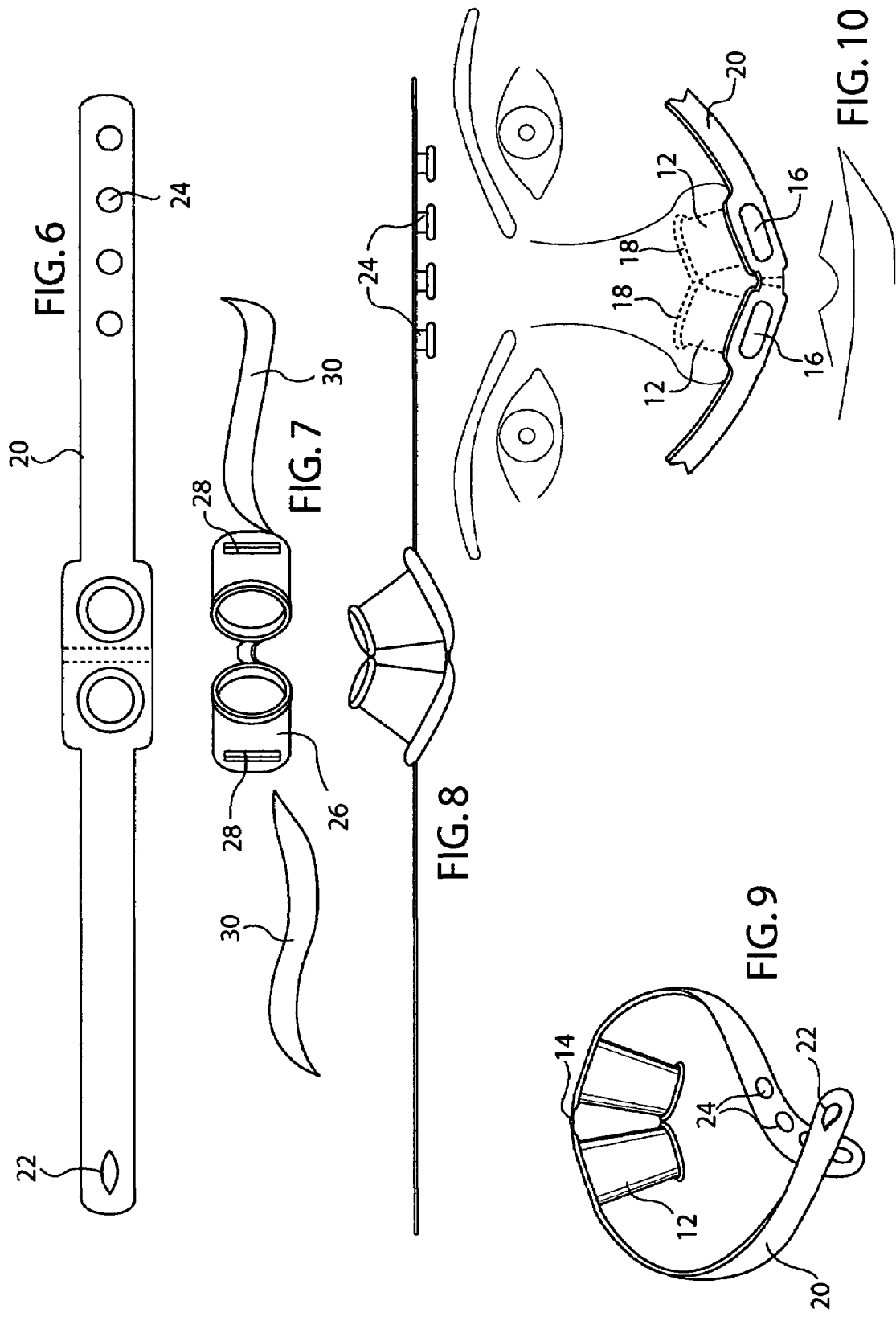

FREE BREATHING APPARATUS

CROSS-REFERENCE TO RELATED APPLICATIONS

A provisional application describing this invention was filed Jan. 20, 2005 and assigned Ser. No. 60/645,515.

STATEMENT REGARDING FEDERALLY SPONSORED RESEARCH OR DEVELOPMENT

Research and development of this invention and Application have not been federally sponsored, and no rights are given under any Federal program.

REFERENCE TO A MICROFICHE APPENDIX

NOT APPLICABLE

BACKGROUND OF THE INVENTION

1. Field of the Invention

This invention relates to nasal breathing assist devices, in general, and to such devices as can be advantageously utilized while exercising, jogging, sleeping or participating in just about any activity, in particular.

2. Description of the Related Art

As will be evident to the broadcast and cable television viewer of college and professional football games, more and more athletes utilize various types of nasal strips while playing to allow greater oxygen intake in efforts to enhance performance while participating. As is also well known and understood, it is not unusual for even a non-athlete to experience difficult breathing at times, whether the result of clogged sinuses, or other maladies. Sleep apnea has gotten more and more attention of late with clinics and specialties being advertised, beyond just snoring at night. While surgery and/or other treatments are regularly recommended, nasal breathing assist devices have been, and are being, proposed on a regular basis to deal with these annoying, or in the extreme life threatening, situations. One such proposal is that described in U.S. Pat. No. 6,562,057 (Santin), available under the Trademark SINUS CONES.

SUMMARY OF THE INVENTION

As will become clear from the following description, the free breathing apparatus of the present invention represents a significant improvement over Santin-SINUS CONES devices in several respects. As will be appreciated, one of the more important features is a redesign which secures its tubular elements within the nasal passages. This follows extensive experience which showed that during active exercising and movement, the tubular elements of that patent experienced a very distinct tendency to come loose and dislodge. Moreover, this became all the more pronounced when the user was possessed of a condition which developed mucous in the nose, leading to the tubular elements loosening because of the increased slippery condition which resulted. Also, the construction of such tubular elements as set out in the '057 patent did not naturally fit the curvature of the nasal passages in which they were inserted, giving rise to an increasing discomfort state as such nasal breathing assist devices were worn for longer and longer time periods.

Secondly, an equally important feature of the redesign is the orientation and utilization of the tubular elements in a manner to further spread the nostrils of the user in enhancing air flow.

As will be seen from the following description, the free breathing apparatus of the invention incorporates a semi-rigid resilient bridge element extending between the tubular elements, to quiescently arrange them at an obtuse angle. As will be appreciated by those skilled in the art, a pressure from the user's fingers is required to bend the tubular elements toward one another for their insertion into the nostrils, which with the subsequent unfurling of the bridge element brings the tubular elements back towards, and hopefully to, their original obtuse angulation to spread the nostrils further apart.

As will also be seen, rather than just inserting the tubular elements into the nostrils in hope that the nasal passages themselves hold the tubular elements in place, or employ further clips on the tubular elements to join them with the external sides of the nose as in the Santin patent, the free breathing apparatus of the present invention utilizes a strap of adjustable length to join with the tubular elements in extending them about the face and back of the head of the user, below the ears. Any type of adjustable securement for the strap can be employed—and, in a construction, where the user could detach the straps from tabs coupled with the sides of the tubular elements for removable connections, if desired.

For providing added comfort when wearing, the tubular elements of the free breathing apparatus of the invention will be seen to be upwardly curvable to slant at its forward-most end, so as to contour more closely with the shape of the nasal passages when inserted forwardly in a downward direction.

As will be appreciated by the skilled artisan, the free breathing apparatus of the invention then widens the nostrils for clearer breathing regardless of the extent of activity being undertaken, while being adjustably secure for an accurate fit when being worn, and in a more comfortable manner once in place.

BRIEF DESCRIPTION OF THE DRAWINGS

These and other features of the present invention will be more clearly understood from a consideration of the following description taken in connection with the accompanying drawings, in which:

FIG. 1 is a bottom view of a preferred embodiment of the free breathing apparatus of the invention as it would appear prior to use;

FIG. 2 is a front side view of the free breathing apparatus of FIG. 1;

FIGS. 3 and 4 are pictorial views helpful in an understanding of how the free breathing apparatus of the invention can be manually fitted about the head of the ultimate wearer, as illustrated in the further pictorial view of FIG. 5;

FIGS. 6 and 7 illustrate different manners of joining the adjustable straps with the tubular elements of the apparatus, with FIGS. 8 and 9 helpful in an understanding as to how the tubular elements are inserted into the nostrils of a user as in FIG. 10, and adjustably secured in place;

DETAILED DESCRIPTION OF THE INVENTION

Figure 11:
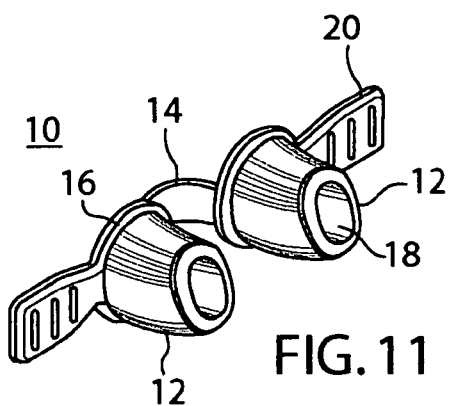
FIG. 11 is a perspective view of an alternative configuration for the tubular elements of the free breathing apparatus.
Figure 12:
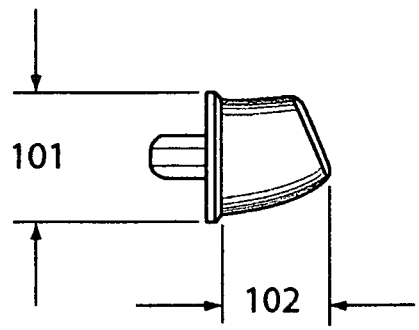
FIGS. 12-14 are mechanical views helpful in an understanding of various dimensionings which have proved useful in the construction of the configuration of FIG. 11.
Figure 13:
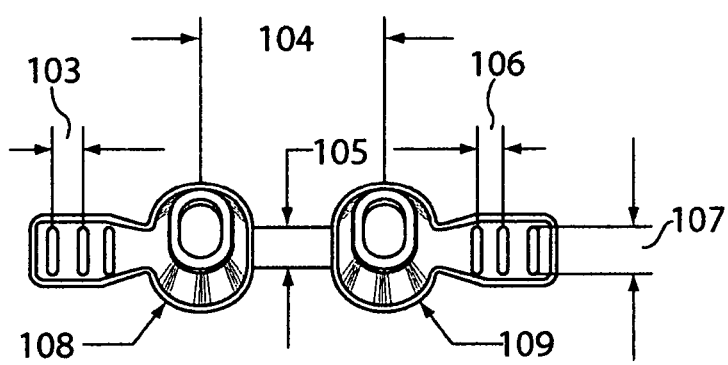
Figure 14:
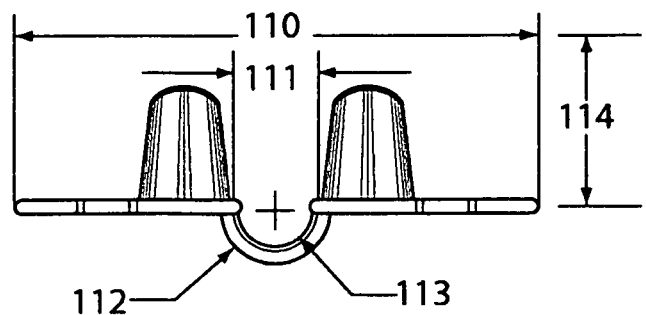
Figure 15:
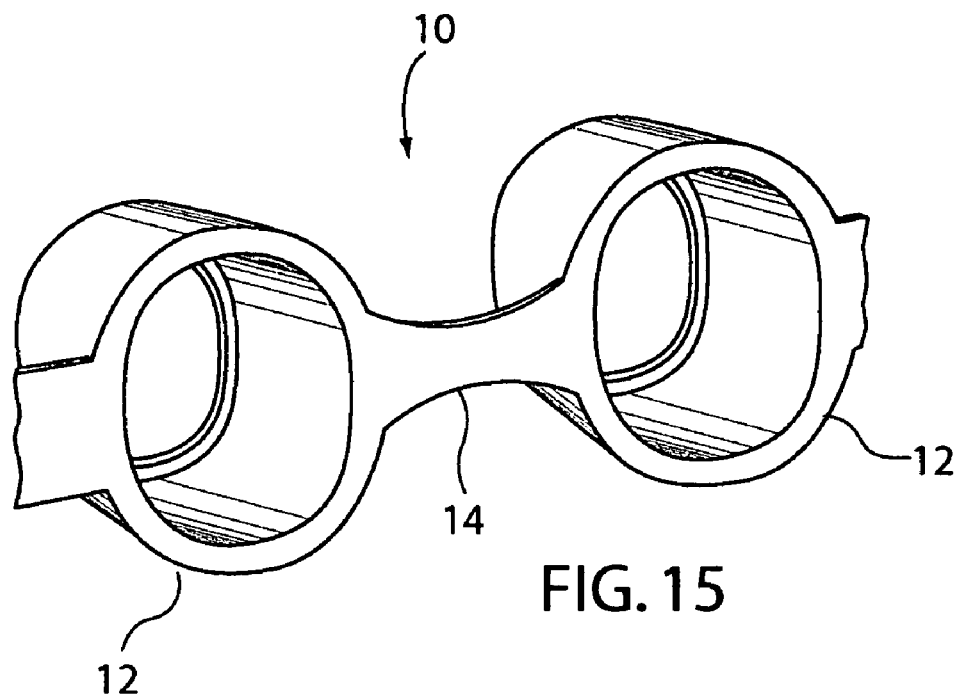
FIGS. 15 and 16 are pictorial front and rear views of the free breathing apparatus of the invention in one form, without the attachment of any adjustable securing straps.
Figure 16:
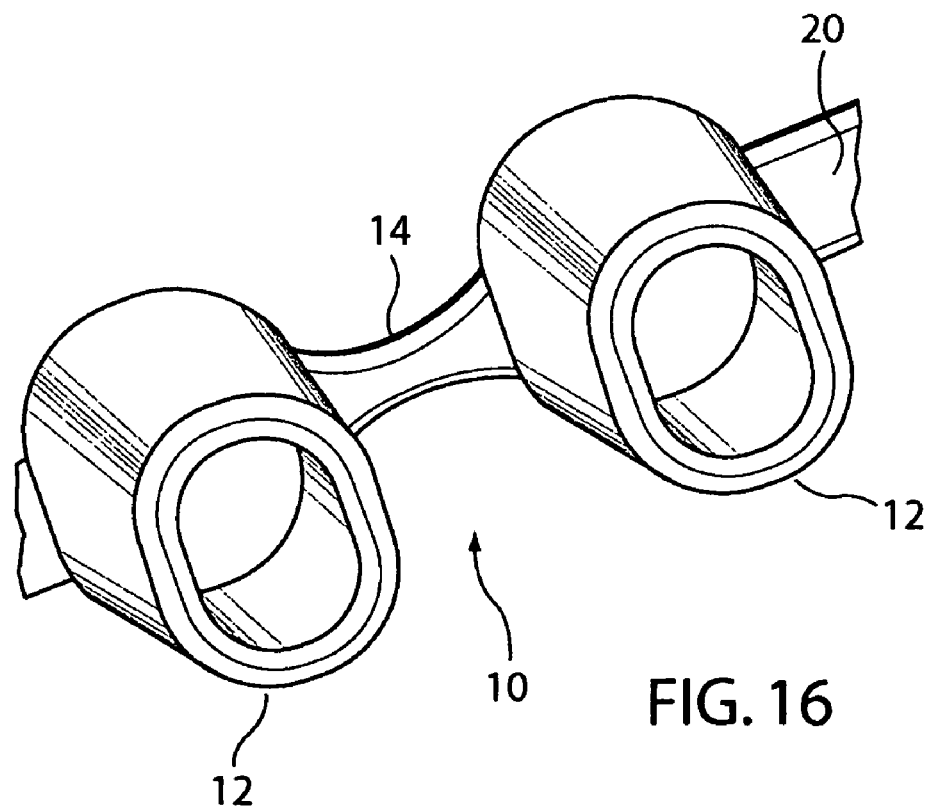

As illustrated in the drawings, and particularly in FIGS. 15 and 16, the free breathing apparatus of the invention 10 includes a pair of open-ended tubular elements 12 connected together at an obtuse angle by a bridge element 14. As with the Santin nasal breathing assist devices, the tubular elements 12 are generally circular in cross-section and extend at this obtuse angle along their respective tube axes from first ends 16 to second ends 18. As shown in FIG. 11, the tubular elements taper curvilinearly upwardly from a relatively large diameter cross-section to a relatively smaller diameter cross-section between the first end 16 and the second end 18. Such upward curvilinearity will be appreciated to provide an enhanced fitting in contouring to the taper inside the user's nostrils.

Figure 4:
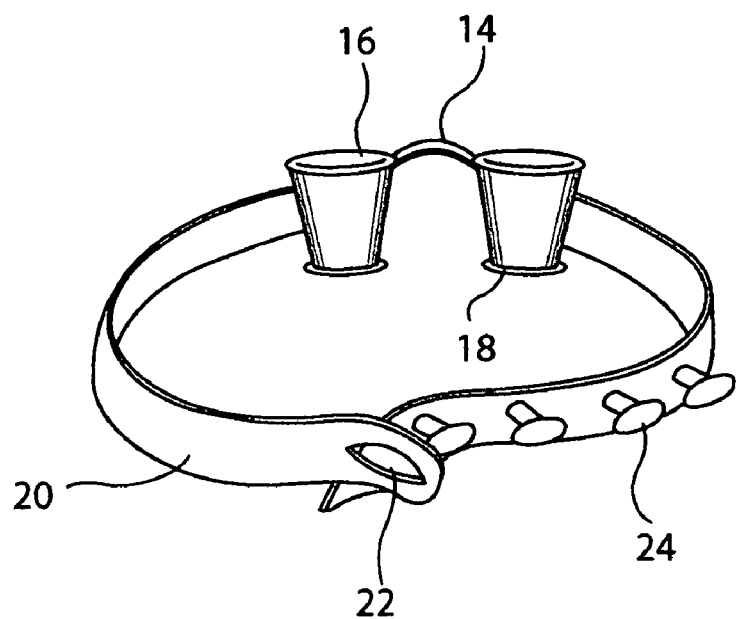
Figure 5:
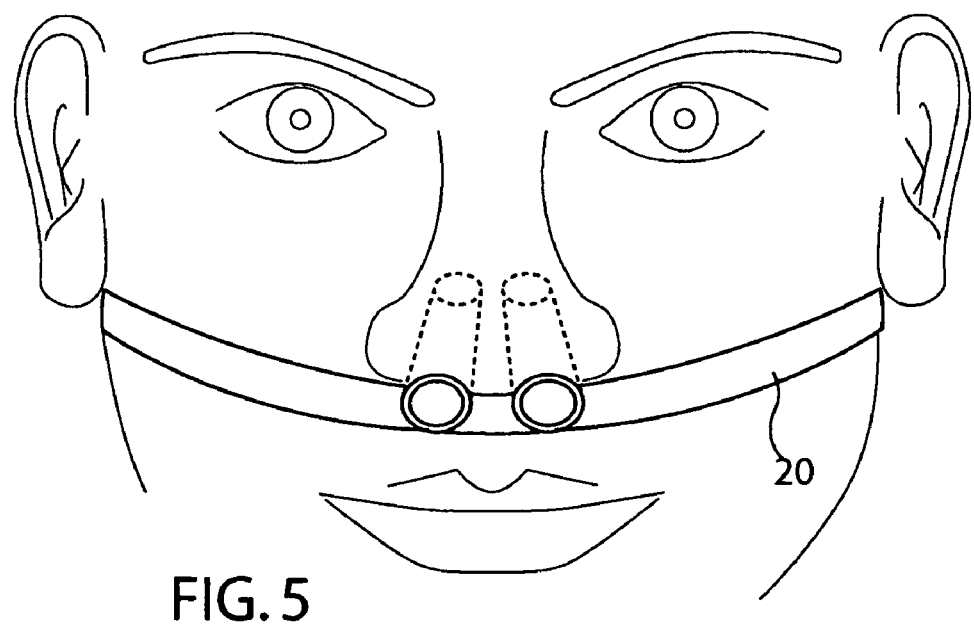

The bridge element 14 will be seen to connect to the first ends 16 of each tubular element 12, to the opposite outside surfaces of which opposing portions of an adjustable strap 20 are secured, as shown in the various drawings. The strap 20 enables the free breathing apparatus 10 to wrap around the face and head of a wearer, to be thusly held in place even though the wearer at the time may be extensively exercising or jogging—or otherwise participating in athletic or other strenuous activities (FIGS. 5 and 10).

As will be appreciated by those skilled in the art, different types of strap securements may be employed utilizing, for example, apertures 22 and projecting nibs 24 as shown in FIGS. 1-2, 4, 6, and 8-9. The straps 20 and tubular elements 12 may be constructed of any appropriate material, such as a soft, flexible rubber, vinyl or latex. The inclusion of several apertures 22 and/or nibs 24 enable the strap 20 to be adjusted in length so as to accurately and comfortably secure the strap 20 about the face, under the ears and around the head.

As FIGS. 15-16, 1-2 and 9 depict, the bridge element 14 is a straight-though resilient bendable link which maintains the tubular elements apart but allows their bending towards and away from one another, as illustrated in FIGS. 2 and 8-10.

The bridge element 14 is a resilient, yet semi-rigid material which maintains the central axes of the tubular elements 12 spaced apart at an obtuse angle, yet with their respective axes being pinchable under finger pressure to move the tubular elements closer together towards forming an acute angle between them. This allows the tubular elements to easily be inserted into the nostrils of the user independent of the lateral size of the nose and the nostril; but because of the resilient nature of the semi-rigid bridge element, also allows through spring-like action, the bridge element to rotate the tubular elements back toward, and hopefully to, the initial quiescent obtuse angle in thereby spreading the nostrils apart after insertion. By pinching the outside surfaces of the tubular elements for insertion, followed by then releasing them, this allows for an easier, clearer breathing.

The embodiment of FIG. 7 illustrates that slotted tabs may be provided at the opposite outside surfaces of the tubular elements 12 for detachable coupling of straps to the free breathing device. Such tabs, slots and strap connections are illustrated at 26, 28, 30 respectively. FIG. 6, on the other hand, shows yet another embodiment of the invention. However, with each such embodiment, as well as with the others illustrated, the advantages of the invention continue: 1) utilizing a strap connection to the tubular elements to allow the breathing apparatus to be wrapped around the face and head when wearing, to prevent its coming loose or falling out during exercising, as well as when just sitting or sleeping; 2) providing an upward curvilinearity to the individual tubular elements to more naturally fit to the contours and curvature of the nasal passages of the nostrils when inserted forwardly in a downward direction; and 3) employing a bridge element coupling between the tubular elements of sufficient rigidity to act as a spring in attempting to rotate the tubular elements once inserted back towards, and hopefully to, their quiescent obtuse angle spread to further separate the nostrils beyond that afforded by a tightening of the securing strap.

While applicant does not wish to be limited to any particular set of dimensions, the following have proved useful in one construction of the preferred embodiment shown in FIGS. 11-14.

| | |
|---|---|
| Dimension 101 | 0.72 inches |
| Dimension 102 | 0.63 inches |
| Dimension 103 | 0.17 inches |
| Dimension 104 | 1.00 inches |
| Dimension 105 | 0.24 inches |
| Dimension 106 | 0.15 inches |
| Dimension 107 | 0.28 inches |
| Radius 108 | 0.30 inches |
| Radius 109 | 0.27 inches |
| Dimension 110 | 2.94 inches |
| Dimension 111 | 0.46 inches |
| Radius 112 | 0.30 inches |
| Radius 113 | 0.20 inches |
| Dimension 114 | 0.55 inches |

In this respect it will be appreciated that the embodiment of the invention shown in FIGS. 11-14 and the embodiments of FIGS. 15-16 are depicted after the tubular elements 12 have already been pinched inwardly for insertion into the wearer's nostrils. The configuration of FIG. 2, on the other hand, illustrates the quiescent condition of the free breathing apparatus of the invention with the obtuse angle spread before such pinching, to which the bridge element 14 seeks to revert the tubular elements once released in the nostrils to spread the nasal passages apart.

While there have been described what are considered to be preferred embodiments of the present invention, it will be readily appreciated by those skilled in the art that modifications can be made without departing from the scope of the teachings herein. For at least such reason, therefore, resort should be had to the claims appended hereto for a true understanding of the scope of the invention.

I claim:

1. A free breathing apparatus comprising:
   a pair of open-ended tubular elements, each extending along a central tube axis between a relatively large first end and a relatively small second end;
   a bridge element extending between said first ends of said tubular elements and oriented therewith of a composition to permit relative rotational motion of the central tube axis of each tubular element from a predetermined quiescent angle for each tubular element with respect to said bridge element to a lesser angle for each tubular element with respect to said bridge element upon the application of a pinching pressure from a user's fingers on opposing side surfaces of each of said tubular elements when inserting said tubular elements into the nasal passages of said user's nostrils, and to permit relative rotational motion of the central tube axis of each tubular element with respect to said bridge element back towards said quiescent angle for each tubular element with respect to said bridge element after insertion of said tubular elements into said nasal passages and release of the user's fingers from said opposing side surfaces of said tubular elements; and a strap coupled between said opposing side surfaces of said tubular elements, said strap being of adjustable length to join with said tubular elements in extension about the face and back of the head of the user, below the ears, in holding said tubular elements in inserted position within said nasal passages when the free breathing apparatus is worn;

with said strap being selectively shortenable to rotate the central tube axis of each tubular element outwardly to an angle with respect to said bridge element which is greater than said quiescent angle of each tubular element with respect to said bridge element;

and with the length of said strap at any instant of wearing and with said predetermined quiescent angle of each tubular element with respect to said bridge element being selected to spread said nasal passages to assist increased breathing ability by the user once said tubular elements are inserted and said strap is in place about the face and back of the head of the user.

2. The free breathing apparatus of claim 1 wherein said bridge element is composed of a semi-rigid resilient material to bend in lessening said quiescent angle of each tubular element upon application of finger pressure to opposing outside surfaces of said tubular elements when inserting said tubular elements into the nasal passages of the nostrils and to return towards said quiescent angle of each tubular element upon release of said finger pressure after insertion.

3. The free breathing apparatus of claim 2 wherein said bridge element is of a semi-rigid resilient material to permit relative rotational motion of said tube axes of each tubular element from a quiescent obtuse angle to a lesser angle and back towards said quiescent obtuse angle of each tubular element in insertion of said tubular elements into the nasal passages of a user's nostrils.

4. The free breathing apparatus of claim 3 wherein said bridge element is of a semi-rigid resilient material to bend in lessening said quiescent obtuse angle of each tubular element upon application of finger pressure to opposing side surfaces of said tubular elements when inserting said tubular elements into the nasal passages of the nostrils and to return towards said quiescent obtuse angle of each tubular element upon release of said finger pressure after insertion.

5. The free breathing apparatus of claim 4 wherein the central tube axes of said tubular elements extend curvilinearly upwardly from said first end to said second end.

6. The free breathing apparatus of claim 2 wherein the central tube axes of said tubular elements extend curvilinearly upwardly from said first end to said second end.

7. The free breathing apparatus of claim 1 wherein said strap includes a plurality of linearly spaced projecting nibs and apertures fitted together to set the shortened length of said strap at any instant of wearing.

8. The free breathing apparatus of claim 7 wherein said projecting nibs extend from said strap in a direction opposite to the direction in which each of said tubular elements extend on opposite sides of said bridge element.

* * * * *